United States Patent [19]
Rawlings et al.

[11] Patent Number: 5,409,472
[45] Date of Patent: Apr. 25, 1995

[54] ADHESIVE POLYMERIC FOAM DRESSINGS

[75] Inventors: David A. Rawlings, Elmdom; Patrick L. Blott, Bishops Stortford, both of United Kingdom

[73] Assignee: Smith & Nephew plc, United Kingdom

[21] Appl. No.: 42,871

[22] Filed: Apr. 5, 1993

Related U.S. Application Data

[63] Continuation-in-part of Ser. No. 688,625, Jun. 11, 1991, abandoned, and a continuation-in-part of Ser. No. 689,232, Jun. 11, 1991, abandoned.

[30] Foreign Application Priority Data

| Aug. 3, 1989 | [GB] | United Kingdom | 8917788 |
| Aug. 3, 1989 | [GB] | United Kingdom | 8917790 |
| Aug. 1, 1990 | [WO] | WIPO | PCT/GB90/01193 |
| Aug. 1, 1990 | [WO] | WIPO | PCT/GB90/01194 |

[51] Int. Cl.$^6$ ............. A61F 13/00; A61F 15/00
[52] U.S. Cl. ............. 604/307; 602/46; 602/55; 602/47; 602/58
[58] Field of Search ............. 602/46, 47, 55, 58, 602/42, 59, 54, 57; 604/307

[56] References Cited

U.S. PATENT DOCUMENTS

| 3,416,525 | 12/1968 | Yememian | 602/47 |
| 4,231,357 | 11/1980 | Hessner | 602/47 |
| 4,323,557 | 4/1982 | Rosso et al. | 424/28 |
| 4,655,210 | 4/1987 | Edenbaum et al. | 602/46 |
| 4,657,006 | 4/1987 | Rawlings et al. | 602/47 |
| 4,926,850 | 5/1990 | Lott et al. | 128/155 |
| 5,018,515 | 5/1991 | Gilman | 128/155 |
| 5,060,642 | 10/1991 | Gilman | 602/57 |
| 5,244,457 | 9/1993 | Karami et al. | 604/307 |

FOREIGN PATENT DOCUMENTS

| 0094755 | 11/1983 | European Pat. Off. | 602/54 |
| 0106440 | 4/1984 | European Pat. Off. | |

*Primary Examiner*—Paul Probilic
*Attorney, Agent, or Firm*—Rosenman & Colin

[57] ABSTRACT

A conformable wound dressing is produced which comprises a polymeric foam absorbent layer, a continuous or discontinuous adhesive layer covering the body facing surface of the absorbent layer except for a wound contacting area which is free of adhesive and a layer of a liquid impervious moisture vapor permeable material disposed over substantially all or the entire surface of the absorbent layer opposite the body facing surface. The wound dressing may have a discontinuous intermediate layer coextensive with the absorbent layer disposed between the absorbent layer and the adhesive layer. Preferably, more than 50% of the absorbent layer is free of adhesive or when the adhesive is placed on the intermediate layer, more than 50% of the absorbent layer and the intermediate layer are free of adhesive.

25 Claims, 4 Drawing Sheets

ADHESIVE POLYMERIC FOAM DRESSINGS

This is a continuation-in-part of our applications Ser. No. 688,625 filed Jun. 11, 1991 and Ser. No. 689,232 filed Jun. 11, 1991, both abandoned.

FIELD OF THE INVENTION

This invention relates to adhesive dressings and particularly to adhesive bandages as would be suitable for first-aid dressings.

BACKGROUND OF THE INVENTION

A prime requirement for first-aid dressings is that they should be highly conformable and pliable since they have to be used for the dressing of highly rounded surfaces such as fingers as well as for flexing surfaces such as knuckles.

Conventionally first-aid dressings are formed as a relatively bulky but small pad of an absorbent material such as gauze layers adhered to a larger backing sheet made of a woven fabric or filmic material. Usually the pad is covered by layers of cover-stock intermediate the pad material on the wound to reduce adherence between the wound eschar and the fibres of the absorbent material.

The manufacturing of such dressings requires need to maintain accurate registry between the coverstock and the pad and the pad and backing layer during the production stage.

Known dressings may also suffer from the disadvantage that, because they are manufactured from highly porous materials, airborne bacteria can enter the dressing and infect the wound. This problem may be further accentuated where the dressings are not waterproof and water-borne bacteria and viruses can enter or leave the dressings.

We have now found that the problems associated with manufacture and bacterial contamination may be reduced by highly pliable and conformable dressings which comprise a composite of coextensive layers.

BRIEF DESCRIPTION OF THE DRAWINGS

FIG. 5b is a plan view of the top of the dressing shown in FIG. 5a;

FIG. 5c is a plan view of the bottom of the dressing shown in FIG. 5a;

FIG. 11b is a plan view of the top of the dressing shown in FIG. 11a;

FIG. 11c is a plan view of the bottom of the dressing shown in FIG. 11a.

SUMMARY OF THE INVENTION

According to the present invention, a conformable wound dressing is constructed which comprises a polymeric foam absorbent layer, a continuous or discontinuous adhesive layer covering the body or wound facing surface of the absorbent layer except for a wound contacting area which is free of adhesive and a layer of a liquid impervious moisture vapor permeable material disposed over either substantially all or the entire surface of the absorbent layer opposite the body facing surface.

The wound dressing alternatively may further comprise a discontinuous intermediate layer coextensive with the absorbent layer disposed between the absorbent layer and the adhesive layer.

The adhesive layer may be confined to the edges of the absorbent layer or the intermediate discontinuous layer so that at least 40% of the absorbent layer is free from adhesive, preferably greater than 50%, more preferably at least 85% of the absorbent layer is adhesive free.

It is preferred that the wound contacting area which is free of adhesive be a single area.

Typically, a single adhesive free area would be located centrally on the body facing surface of the dressing and would constitute the wound contacting surface. The adhesive surrounding this wound contacting surface of the absorbent or intermediate layer would secure the dressing to the intact skin around the wound.

Normally, the layers of the dressing are attached in a contiguous manner so as to form a laminate.

DETAILED DESCRIPTION OF THE INVENTION

According to one embodiment of the present invention, the opposed margins are substantially thinner than the region between the dressing. This feature not only enhances the conformability of the dressing since the flexural rigidity of the dressing is reduced at the margins but also minimizes the risk of the dressing being caught at the edge and inadvertently lifted.

The term "opposed margins" not only encompasses those embodiments where there are margins on separate, clearly defined edges forming the perimeter of the dressing but also those embodiments where there is a single continuous margin around the perimeter of the dressing and no discernible edges, e.g., the perimeter of a circular or oval dressing. In the latter case, "opposed margins" refers to the margin at opposed points or positions on the dressing. Thus, for circular dressings the opposed margins are the margins at diametrically opposed positions.

The thickness of the opposed margins of the absorbent layer should preferably be no greater than two-thirds of the thickness of the layer between the margins. More preferably, the thickness of margins should be less than half the thickness of the layer between the margins. The thickness of the dressing may be reduced step-wise or continuously towards the edge margins. For example, the material comprising the absorbent layer may have chamfered edges.

According to a preferred embodiment of the present invention, the adhesive free area is a single area located on the thicker portion of the body or wound facing surface of the absorbent layer and preferably is centrally located.

For dressings, suitable for use as first-aid bandages, the thickness of the foam-containing layer in the region between the edges may be up to about 5 mm thick, preferably up to about 2.5 mm thick. For specialist applications or for larger dressings such as ward dressings, the thickness of the region between the edges may be greater than 5 mm for example up to 2.5 cm. The thickness of the edges may, for the dressing of the invention be no greater than about 10% of the thickness of the intermediate region.

Wound dressings of the invention can suitably have a moisture vapour transmission rate (MVTR) of at least 300 grams/m$^2$/24 hrs at 37.5° C. at 100% to 10% relative humidity difference. Typically, the MVTR will be between 300 to 5000 and preferably at least 500 preferably 500 to 2000 grams/square meter/24 hours at 37.5° C. at 100% to 10% relative humidity difference when in contact with water vapour but not liquid water. It has been found that such moisture vapour transmission rates will allow the wound under the dressing to heal under moist conditions without causing the skin surrounding the wound to macerate.

The moisture vapour transmission rate as determined in contact with water vapour but not liquid water and is determined as follows:

Discs of the material under test are clamped over Payne Permeability Cups (flanged metal cups) using sealing rings and screw clamps. The exposed surface area of the test sample is 10 cm$^2$. Each cup contains approximately 10 ml of distilled water.

After weighing, the cups area placed in a fan assisted electric oven which is maintained at 37°±1° C. The relative humidity within the oven is maintained at approximately 10% by placing 1 Kg of anhydrous 3–8 mesh calcium chloride on the floor of the oven.

The cups are removed after a predetermined period of time allowed to cool for 20 minutes and reweighed. The MVTR of the test material is calculated from the weight loss and expressed in units of grams of weight per square meter per 24 hours.

The adhesives employed in the present invention are suitably those which do not adhere to the moist surface of the healing wound. The adhesive on the wound facing surface of dressings of the invention then allows these dressings to be adhered to the skin around the wound site.

The adhesive may be applied as a coating on the absorbent layer or on an intermediate discontinuous layer. In another embodiment the adhesive may be formed in situ on the intermediate or absorbent surfaces, e.g., by the polymerization of a non-adhesive monomeric precursor.

The adhesive may be a discontinuous layer or more preferably a continuous layer. A discontinuous layer may be randomly distributed, for example, as spots or as a layer of a porous adhesive. Alternatively, the adhesive may be a regularly patterned discontinuous layer in the form of regularly arranged spots or lines or in a grid arrangement.

Where the adhesive is coated on to the discontinuous intermediate layer, the adhesive may be a continuous coating on the surfaces of the intermediate layer. The adhesive layer will become discontinuous, and the discontinuities will register with the discontinuities in the intermediate layer.

In a further embodiment of the invention, it is desirable that adhesive be present at the edges of the dressing. However, the adhesive layer need not be over the entire wound facing surface of the absorbent or intermediate layer and need not be coextensive with the absorbent layer. In this embodiment, the adhesive layer may comprise a continuous or discontinuous adhesive coating or layer wherein the absorbent layer is largely free of adhesive. The adhesive may be colored differently from that of the absorbent layer or intermediate layer to provide a visual distinction. The absorbent layer or intermediate layer will therefor be the direct wound-contacting portions with a peripheral layer of adhesive for securing the dressing to intact tissue.

It is preferred that at least 10% of the wound facing surface of the absorbent or intermediate layer be covered with adhesive and that the adhesive be present at all the peripheral regions of the wound facing layer.

Suitable adhesive layers for the wound facing layer of dressings of the invention have a thickness of at least 15 microns and may more aptly be from 15 to 75 microns, preferably from 25 to 50 microns. Suitable adhesives for the wound facing layer can be any of those pressure sensitive adhesives normally used for adhesive surgical or medical dressings. Preferred pressure sensitive adhesives comprise acrylate ester copolymers and polyvinyl ethyl ether adhesives, such as those disclosed in United Kingdom Patent Specification No. 2070631 and European Patent Specification Nos. 0099675 and 0194881.

The material employed for the discontinuous layer intermediate the adhesive and the foam absorbent layer may be a conformable elastomeric film provided with apertures or may be a plurality of conformable elastomeric polymer strands laid down to a net of desired shape, size and configuration. In another embodiment, the discontinuous layer may be formed from a nonwoven material.

Aptly, the discontinuous layer is formed from a polymeric film. The film may be perforated, apertured or cut to provide discontinuities. Alternatively, the film may be subjected to physical treatments to form a net.

The conformable elastomeric discontinuous film or net allows wound exudate to pass to the absorbent foam layer but prevents the absorbent layer making direct contact with the wound surface.

Preferably, the discontinuous layer used in this invention is an integral net, that is, a net with strands and junctions which have been formed integrally from a unitary film during manufacture.

Preferably, the discontinuous layer is sufficiently conformable to allow the wound dressing to conform with the body contours and thereby maintain overall contact with the wound surface to ensure that exudate from the wound is absorbed.

It is also desirable that the discontinuous layer should be sufficiently elastically extensible to adjust to any dimensional changes in the absorbent layer which may occur, for example, by expansion on liquid uptake.

Suitable discontinuous layers will have elongation at break of 100% to 800%, desirably 200% to 750%, and preferably 300% to 700% when measured as a 2.5 cm wide strip at a 30 cm/minute strain rate at 20° C.

Normally the discontinuous layer of elastomer is made of a pharmaceutically acceptable water insoluble elastomer.

Suitable elastomers for use in manufacturing the discontinuous layer include polyurethanes, polybutadiene and the like. Such elastomers may be present as block copolymers with other polymer constituents.

The preferred material for the nets are thermoplastic polyurethanes.

Polymer blends having a continuous phase of an elastomer and a discontinuous or discrete phase of a polymer which is incompatible with the elastomer may also be used for the discontinuous intermediate layer, e.g., net. Suitable polymer blends include blends of elastomers such as polyurethanes or ethylene-vinyl acetate copolymers as the continuous phase and incompatible polymers such as an olefine or an aromatic hydrocarbon, for example, polystyrene.

Preferred thermoplastic polyurethanes are linear polyurethanes containing polyether or polyester groups. Suitable linear polyester polyurethanes are disclosed in U.S. Pat. No. 2,871,218. Suitable linear polyether polyurethanes are disclosed in U.S. Pat. No. 2,899,411. Favored thermoplastic polyurethanes include Estane brand polyurethane from B. F. Goodrich Corp. Preferred solution casting grades are Estane 5714F1, 5702 and 5703. A preferred extrusion grade is Estane 580201.

Suitable polybutadienes are 1,2 polybutadienes. Favored 1,2 polybutadienes contain a major amount of syndiotactic 1,2 polybutadiene, have a crystallinity of 25% to 30% and an average molecular weight in excess of 100,000. Preferred 1,2 polybutadienes are known as RB 810, RB 820 and RB 830 made by Japan Synthetic Rubber Company.

The net of the discontinuous layer of the dressing can have any convenient form depending on the chosen arrangement of strand, junctions and aperture areas and also their shapes and relative size.

The number and size of the apertures in the net will be sufficient to allow the wound exudate to pass through the film to the absorbent layer. Most aptly, the net is adapted so that the size of apertures in combination with the thickness of the film prevent the absorbent layer contacting the wound surface. The nets can have apertures with a dimension of at least 0.05 mm. Generally, the aperture size can be up to 4 mm. Suitable nets have apertures with a dimension of from 0.05 to 4 mm, more aptly from 0.05 to 2.5 mm or 0.05 to 2.0, and preferably from 0.1 to 2.5 mm. The net thickness may be greater than 0.01 mm. Net thicknesses of up to 2.5 mm may be aptly used. Thus a suitable net can have a thickness of 0.01 to 2.5 mm, typically of 0.01 to 0.25 mm, and preferably of 0.05 to 0.5 mm. Favored nets of the invention have 4 to 40 apertures per cm with dimension of 0.05 to 2.5 mm. The wound face of the net will have 15 to 80% of its area void (the apertures), more suitably will have 25 to 75% of its area void, and most suitably will have 35 to 65% of its area void.

The net of the wound dressing of the invention can have any convenient form depending on the chosen arrangement of strand, juncture and hole areas and also their shapes and relative size.

In one preferred form the net consists essentially of longitudinal and transverse strands intersecting at right angles to give a square grid hole pattern.

Suitable nets of this type aptly have 2 to 50 strands per cm, desirably 4 to 40 strands per cm, and preferably 2 to 24 strands per cm in both longitudinal and transverse directions.

Variations on the square grid pattern can give other desirable forms of the integral net. Unequal density of strands in either the longitudinal or transverse directions will give rectangular hole areas. Continuous parallel strands in one direction with a staggered arrangement of connecting strands in the other direction will give a "brick-work" pattern. Other apt forms of the integral polymer nets can have strands at an angle to the longitudinal or transverse direction (that is, diagonal strands). Another preferred form of the integral polymer net can have a staggered arrangement of circular or approximately circular (for example hexagonal) arrangements of strands and hole areas. The integral polymer net can be in the form of a mixed pattern of two or more of the arrangements if desired.

The apertured film or net used in this invention aptly will have a weight of at least 10 gsm and may have a weight of from 10 gsm to 80 gsm, preferably from 15 gsm to 50 gsm.

The adhesive layer or combination of adhesive and discontinuous layer is preferably distensible such that distortion of the dressing does not occur during dimensional changes in the absorbent layer which may occur, for example, by expansion in liquid uptake or on body surface movement, e.g., flexing or stretching over a knuckle or elbow.

The absorbent employed in the absorbent layer of the dressings of the present invention is a polymer foam. The foam is preferably a highly conformable hydrophilic foam, more preferably an open celled foam.

The conformable hydrophilic polymer open cell absorbent layer used in dressings of the invention is capable of absorbing wound exudate. It is desirable that the hydrophilic polymer form layer absorbs the wound exudate rapidly as this enhances the low adherency properties of the absorbent pad. Such rapid absorption prevents undesirable pooling of exudate between the dressing and the wound.

The ability of open cell hydrophilic polymer foam layers to absorb and retain fluids depends to some extent on the size of the foam cells, the porosity of the foam and the thickness of the foam layer.

Suitable open cell hydrophilic foams of dressings of the invention have a cell size of in excess of 30 microns. Generally, the foams will have cell sizes of less than 700 microns. Thus foams having a cell weight of 30 microns to 700 microns may be aptly used. Preferably, the cell size of the foam will be from 50 microns to 500 microns. Apt open cell hydrophilic foams of dressings of the invention have at least 20% and aptly from 20% to 70%, preferably 30% to 60% of the total membrane area of the cells as membrane openings. Such open cell foams permit transport of fluid and cellular debris into and within the foam.

Apt foams may be polyurethane, carboxylated butadiene styrene rubber, polyacrylate or the like foam. Such foams may be made of hydrophilic materials per se or may be treated to render them hydrophilic, for example with surfactants. It is much preferred to use foams which are made of a polymer which is itself hydrophilic as it has been found that the exudate is less likely to coagulate rapidly.

The use of such foams of hydrophilic polymer in the absorbent pad of dressings of the invention can allow the wound to be maintained in a moist condition even when the exudate produced has been absorbed and removed from the wound surface.

Favored hydrophilic polymer foams are hydrophilic polyurethane and especially those which are made of cross-linked hydrophilic polyurethane. Preferred foams can be made by reacting a hydrophilic isocyanate terminated polyether prepolymer with water.

Suitable hydrophilic polyurethane foams of this type include those known as Hypol (trademark) foams. Hypol foams can be made from Hypol hydrophilic prepolymers marketed by W. R. Grace and Co.

The conformable hydrophilic polyurethane foam can be made by mixing together an isocyanate terminated polyether having functionality of more than two with a surfactant and water and casting the mixture onto a surface. This surface advantageously may be the intermediate discontinuous layer.

Preferred isocyanate terminated polyethers include Hypol FHP 2000, 2001, 3000, 3001, 2002 and 2000HD marketed by W. R. Grace and Co. Hypol is described in a booklet published by W. R. Grace and Co. "Hypol: foamable hydrophilic polymers—laboratory procedures and foam formulations". Their preparation and use are disclosed in British Patent Specifications Nos. 1429711 and 1507232.

Suitable surfactants for forming conformable hydrophilic polymer foams include non-ionic surfactants. Favored non-ionic surfactants are oxypropylene-oxyethylene block copolymers known as Pluronic (trademark) marketed by BASF Wyandotte. Preferred Pluronic surfactants include L65, F87, P38, P75 and L62. Another favored non-ionic surfactant is a polyoxyethylene stearyl ether known as Brij 72 (trademark) marketed by Honeywell Atlas.

To prepare a suitable foam, 100 parts by weight of Hypol FHP 2000, 2001, 3000, 3001, 2002 or 2000HD is mixed with 0.3 to 7 parts by weight of surfactant or mixtures of surfactants and 30 to 300 parts by weight of water and the foaming mixture cast onto a surface. Typical foaming mixtures have a cream time of about 20 secs., a rise time of about 250 secs. and a cure time of about 400 secs.

A preferred foam for use in the absorbent layer of the dressings of the invention is disclosed in our United Kingdom Patent Specification No. 2188055 which inter alia there is described a hydrophilic polyurethane foam comprising residues derived from a polyalkylene glycol mono alkyl or mono alkaryl ether. Such foams can be formed by reacting with water the reaction product of polyisocyanate which has a functionality of greater than 2 and polyalkylene glycol mono alkyl or alkaryl ether.

Preferred polyalkylene glycol mono alkaryl ethers are those in which the alkylene group contains up to 4 carbon atoms. More preferably the alkylene group is ethylene.

Suitable polyalkylene glycol mono alkyl ethers for forming the reaction product are those in which the alkyl group contains 1 to 20 carbon atoms. Alkylene favored ethers are those in which the alkyl group is a methyl group. Another class of preferred polyalkylene glycol mono alkyl ethers are those in which the alkyl group contains 10 to 18 carbon atoms, e.g., lauryl or cetyl.

Suitable polyalkylene glycol mono alkaryl ethers include those in which the aryl moiety is phenyl. Preferred ethers are those in which the alkyl moiety contains from 1 to 20 carbon atoms, e.g., octyl or nonyl.

The polyalkylene glycol mono alkyl or alkaryl ether can suitably have an average molecular weight of 180 to 6000. Suitable ethers for forming reaction products used to prepare flexible foams of the invention have an average molecular weight of 180 to 1300 and preferably have an average molecular weight of 350 to 1000.

Suitable ethers for forming reaction products used to prepare stiff foams of the invention have an average molecular weight of 1500 to 6000 and preferably have an average weight of 3000 to 5000.

Apt ethers are polyethylene glycol mono lauryl ethers having an average molecular weight of approximately 1090 and 360 known as Brij 35 and Brij 30, respectively, available from Honeywell Atlas and polyethylene glycol mono methyl ethers having an average molecular weight of approximately 500 and 5000, known as PEG monomethylether molecular weight 550 and 5000, respectively, available from Aldrich Chemicals.

Suitable polyethylene glycol mono nonyl phenyl ethers are commercially available under the trade names Antarox CO-320 and Antarox CO-990. Apt polyethylene glycol mono nonyl phenyl ethers, having an average molecular weight of approximately 440 and known as Antarox CO-520 and CO-990, respectively, available from GAF (Great Britain) Co. Limited.

The polyethylene glycol mono alkyl or alkaryl ether used in the invention will normally contain water. It is preferred, however, that the ether contain less than 1% by weight of water to limit the number of urea groups formed in the reaction with the polyisocyanate.

The polyisocyanate used for forming the reaction product will have a functionality greater than 2, for example, 2 to 5 and will preferably have a functionality of 2.2 to 3.5. Suitable polyisocyanates include aliphatic and aromatic polyisocyanates. Preferred polyisocyanates are aliphatic polyisocyanates. Aliphatic polyisocyanates are usually liquid at ambient room temperature and therefore are convenient to use in a liquid reaction mixture. An apt aliphatic polyisocyanate for use in the invention is a biuret of 1,6 hexamethylene diisocyanate which has a functionality of 2.6, known as Desmodur N100 (trademark) available from Bayer A. G.

Favored aromatic polyisocyanates for forming the reaction product are polymeric methylene diisocyanates. Polymeric methylene diisocyanates comprise a mixture of 4,4'-diphenyl methane diisocyanates and one or more of polymeric homologues. Apt polymeric methylene diisocyanates are known as SUPRASEC VM 20, (trademark) VM 50, DND and VM 90, available from ICI, and have a functionality of 2.13, 2.49, 2.70 and 2.90, respectively.

The reaction product suitable for use in the invention can be a reaction product of one or more polyisocyanates and one or more polyalkylene glycol mono alkyl or aryl alkyl ethers, including mixed alkyl and alkaryl ethers. The reaction product may advantageously be formed using a chain extender.

Suitable chain extenders for use in forming the reaction product include ethane diol, 1,3 propane diol and 1,4 butane diol.

The conformable moisture vapour transmitting outer layer of dressings of the invention can be continuous or discontinuous.

A preferred moisture vapour transmitting outer layer is a continuous conformable film. The continuous moisture vapour transmitting conformable film outer layer of the wound dressing of the invention may be used to regulate the moisture loss from the wound area under the dressing and also to act as a barrier to bacteria so that bacteria on the outside surface of the dressing cannot penetrate to the wound area.

Suitable continuous conformable films will have a moisture vapour transmission rate of 300 to 5000 grams, preferably 500 to 2000 grams/square meter/24 hrs at 37.5° C. at 100% to 10% relative humidity difference. It has been found that such moisture vapour transmission rate of the continuous film allows the wound under the dressing to heal under moist conditions without causing the skin surrounding the wound to macerate.

Suitable moisture vapour transmitting continuous films can be made of polyurethane or copolymers of alkoxy alkyl acrylates or methacrylates such as those disclosed in British Patent No. 1280631. Apt polyurethanes and polyurethane films, particularly highly moisture vapour permeable polymers and foams are also disclosed in European Patent Specification No. 0091800.

The continuous moisture vapour transmitting film can be a conformable polyurethane incompatible polymer blend film containing voids. Suitable conformable polyurethane blend films are disclosed in United Kingdom Patent Application GB 2081721A. A preferred film is formed from a blend of polyurethane and high impact polystyrene.

An apt conformable moisture vapour transmitting outer layer comprises a microporous film. The conformable film microporous outer layer of the wound dressing of the invention may be used to regulate the moisture loss from the wound area under the dressing and also to act as a barrier to bacteria to delay or prevent bacteria on the outside surface of the dressing penetrating to the wound area.

Suitable conformable microporous films will have a moisture vapour transmission rate of at least 300 and aptly from 300 to 5000 grams, preferably at least 500 preferably 500 to 4000 grams/square meter/24 hrs at 37.5° C. at 100% to 10% relative humidity difference.

Suitable conformable microporous films have pore diameter of less than 2 microns desirably less than 0.6 microns and preferably less than 0.1 microns. Such microporous films should have pore diameter of greater than 0.01 microns.

Suitable conformable microporous films may have a thickness of greater than 25 μm. Apt films may have a thickness of less than 400 μm. Thus suitably the thickness of the film will be from 25 to 400 microns, preferably 50 to 300 microns. Generally, the conformable microporous film will be made of a polymer.

Suitable polymers include polyether-polyamide copolymers such as those marketed under the name PEBAX (ATCOCHEM SA) containing a particulate filler (e.g., chalk), plasticized polyvinyl chloride, polyurethane elastomers and ethylene vinyl acetate copolymer elastomers.

A favored conformable microporous film comprises a microporous plasticized polyvinyl chloride film having an average pore diameter of less than 2 microns, a thickness of 250 to 300 microns and a moisture vapour transmission rate of 3000 to 5000 g/m²/24 hours at 37.5° C. at a relative humidity difference of 100% to 10% relative humidity.

The conformable moisture transmitting outer layer of wound dressings of the invention may also comprise a moisture vapour transmitting adhesive layer to bond the outer layer to the layer of open cell foam. The adhesive layers can be continuous or discontinuous.

Suitable adhesives which are moisture vapour transmitting as a continuous layer include various acrylate ester copolymer and polyvinyl ether pressure sensitive adhesives, for example, as disclosed in British Patent No. 1280631. Favored pressure sensitive adhesives comprise copolymers of an acrylate ester with acrylic acid, for example, as disclosed in United Kingdom Application GB 2070631.

The wound dressing of the invention can contain a topically effective medicament. Most suitably, the medicament is an antibacterial agent. Preferably, the antibacterial agent is a broad spectrum antibacterial agent such as silver salt, for example, silver sulphadiazine, an acceptable iodine source such as povidone iodine (also called polyvinyl pyrrolidone iodine or PVP/I), chlorhexidine salts such as the gluconate, acetate, hydrochloride or the like salts or quaternary antibacterial agents such as bensalkonium chloride or the like.

The medicament can be located in the foam layer or in the adhesive coating.

The medicament is preferably located in the foam layer of the dressing.

Preferred amounts of suitable medicaments for incorporation into the foam layer of the dressing of the invention are disclosed in the aforementioned patent specifications.

The foam in the absorbent layer may also contain a superabsorber. Suitable superabsorbers are well known and can include starch and other cellulosic materials such as cross-linked methyl cellulose, as well as known materials containing acrylic unsaturation.

The thinner margins of the dressing may comprise as little as 10% of the total dressing surface area. However, the margins may comprise up to, for example, 90% of the total dressing body contacting surface area and may typically comprise from 20 to 60% of dressing body contacting surface.

In one arrangement, the adhesive layer may be arranged to cover only the thinner marginal regions of the dressing, a centrally disposed adhesive free area of the body contacting surface being in register with the thickened area of the absorbent layer and defining an adhesive free wound contact area.

The width of the margin need not be the same around the whole periphery of the dressing. For example, a generally rectangular or oblate dressing may have opposed margins on one axis which are wider than the margins on the minor axis. As an illustration, a rectangular dressing having body contacting dimensions of 10 cm×2 cm may have a centrally disposed thickened region measuring 6cm×1 cm, the margins of the major axis being 3 cm wide whilst those on the minor axis being only 0.5 cm wide. In this way, the conformability of the dressing is not compromised since the thickened area of the absorbent layer is restricted to the cushioned wound contacting part of the dressing and the thinner edges which bear the majority of the adhesive layer can function to provide the anchorage for the dressing. Dressings of this construction have advantages where, for example, the dressing is applied to a finger, and the ends of the dressing overlap each other. The total thickness of the overlapped regions of the dressing is therefore reduced to a minimum.

The wound dressing of this invention may be in any convenient form of shape or size. In a preferred form, the wound dressing is a pad of rectangular, oval or circular shape. In another preferred form, the wound dressing can be an elongated strip which may be used as a bandage or may be used to prepare smaller dressings. The dressings may also be of irregular shape for use on flexing or bending surfaces such as knuckles, knees and elbows.

Although the dressings of the invention are suitable as first-aid dressings or bandages, they also have use as medical or ward dressings.

The dressings of the present invention have a primary use in the field of first-aid and may be employed in the home and workplace for the primary dressing of wounds and contusions which may cause minor bleeding such as cuts and abrasions, which do not produce large amounts of wound exudate.

The dressings may be supplied in a variety of shapes and sizes for the dressing of lesions ranging from small cuts, for example on the finger, to large skin grazes on, for example, the elbow or knee. The dressings may be square, rectangular, round, oval or oblate in shape. The dressings may be of a specialized shape, for example having a number of fingers extending from a main or central wound contacting region for the dressing of wound on the knuckle. The central part of the dressing is placed over the wound on the knuckle and the fingers, which have adhesive on the body facing surface and the finger portion adhered to the adjacent fingers and back of the hand.

The dressings of the present invention will generally have a flat profile. However, it may be desirable for the central region, which will be placed over the wound, to be thicker than the margins. The thickness of the marginal regions may be reduced to ensure maximum conformability. The edges of the dressing may be chamfered or feathered. This reduces the possibility that the adhered dressing will 'catch' and be lifted.

Dressings of this configuration allow the hand to flex naturally and freely without the risk of the dressing becoming detached.

The overall dimension of dressings or adhesive bandages in accordance with the invention may be as small as 1 cm×1 cm up to 10 cm×10 cm. Alternatively, the dressing may be supplied in roll form, with the adhesive preferably disposed along the major edges of the roll and the central area between the adhesive coated margins free of adhesive.

The dressings of the present invention may also be employed as wound dressings for the dressing of wounds and lesions which do not produce large amounts of exudate. Such dressings have application as post-operative dressings for the covering of closed surgical incisions and for wounds treated in hospital casualty units, which require protection but are bleeding profusely or producing large amounts of exudate.

Such wound dressings tend to be of a larger size than those dressings used for first-aid application in the home and workplace. Wound dressings may be required in sizes ranging from that of the larger first-aid dressing up to, for example, 50 cm×20 cm.

It is desirable that the wound dressing of this invention is sterile. The wound dressing of the invention is advantageously provided in bacteria impervious pouches. Such packed forms can be prepared under aseptic conditions or alternatively sterilized after packing by a conventional procedure. A favored sterilization procedure is heat sterilization, for example by steam. Other favored procedures are ethylene oxide sterilization or gamma irradiation.

In another aspect, the present invention provides a process of making a wound dressing of the invention which comprises bringing together a layer of a liquid impervious moisture vapour permeable layer, an absorbent layer comprising polymeric foam and wound facing layer with adhesive on its wound facing surface.

The absorbent layer may be produced by foaming a suitable polymer into a mould to produce the desired shape by casting into a block and cutting the desired shape before combination with the other components or casting with the other components and then cutting.

Normally, the bringing together of the layers will be a lamination process. Such lamination processes can also be used to form wound dressings with a conformable moisture vapour transmitting outer layer.

The adhesive can be coated onto the wound facing surface of the discontinuous layer before, during or after the layer has been laminated to the foam layer or directly onto the wound facing surface of the foam. In a preferred process, the adhesive in a flowable state is cast into the recesses of a release coated surface having a pattern of discrete raised areas and interconnected recessed areas and the net layer formed in a similar manner on the adhesive layer.

Preferred casting surfaces are embossed polymer sheets. Suitable embossed polymer sheets are disclosed in the aforementioned patents and published patent applications.

The adhesive surface of wound dressings of the invention will usually be provided with a release coated protector. The release coated protector can be the embossed sheet carrier used for forming the adhesive coated net layer. Other suitable release coated protectors include silicone coated release papers such as Steralease paper nos. 15 and 67 made by Sterling Coated Papers Limited.

The dressings of the invention may be readily manufactured by continuous production techniques. Thus, a moisture vapour permeable film and a polymer net may be run in together through the nip of two rollers or a single roller and a flat bed and a polyurethane foam injected into the nip between the film and net. The foam may be formed in situ at the point of injection by mixing a suitable isocyanate prepolymer as hereinbefore described with, for example, water. After curing of the foam is completed, the embossed composite may then be transfer coated with a suitable adhesive, pre-coated on a releasable carrier sheet. Once the adhesive has been transferred and the carrier sheet removed, protector papers for the adhesive may be run onto the adhesive surface, according to conventional techniques. Finally, the dressing may be stamped out by cutting through the composite and the individual dressings packaged.

If desired, the dressings may be sterilized during or at the completion of the manufacturing and packaging process.

DETAILED DESCRIPTION OF THE DRAWINGS AND THE PREFERRED EMBODIMENT

Referring to FIGS. 1 to 5d, a polymeric foam absorbent layer 2 of a dressing 1 is provided with a thickened central region 21 and thinner edge or marginal regions 22. On the top surface of the foam layer 2 is a sheet of liquid impervious water vapour permeable material 3.

Figure 1:
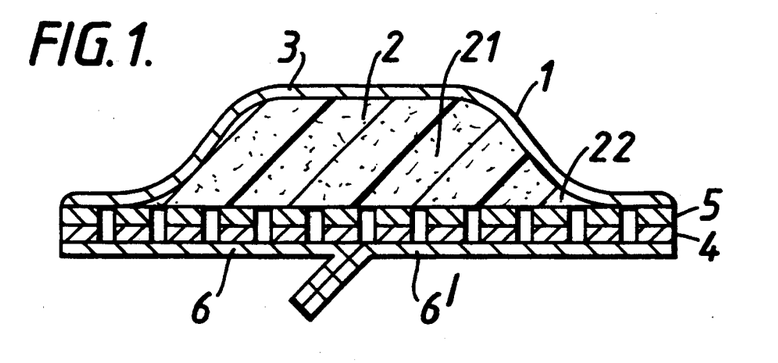
FIG. 1 is a schematic cross-sectional view of an embodiment of the present invention.
Figure 2:
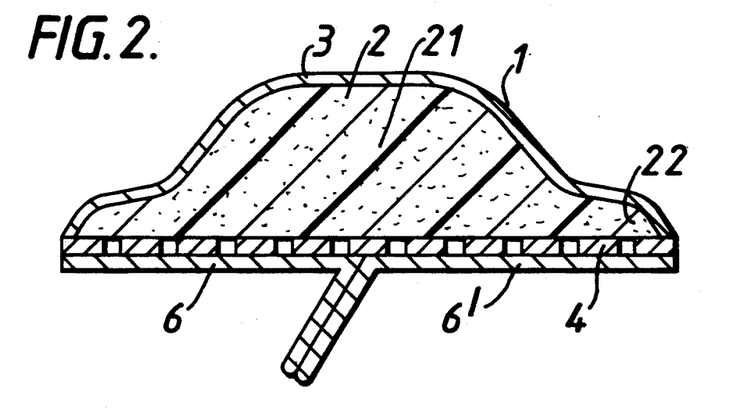
FIG. 2 is a schematic cross-sectional view of another embodiment of the present invention.
Figure 3:
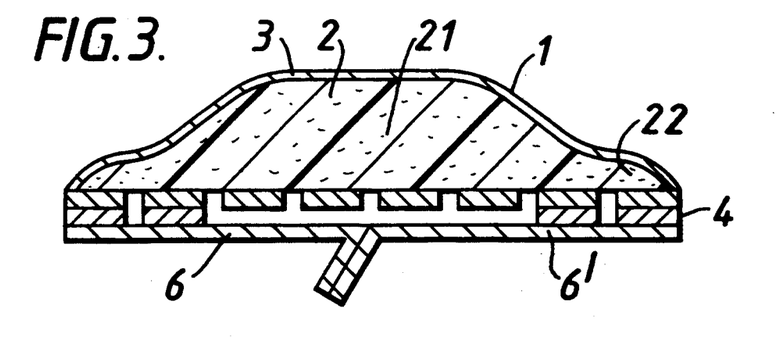
FIG. 3 is a schematic cross-sectional view of another embodiment of the present invention.
Figure 4:
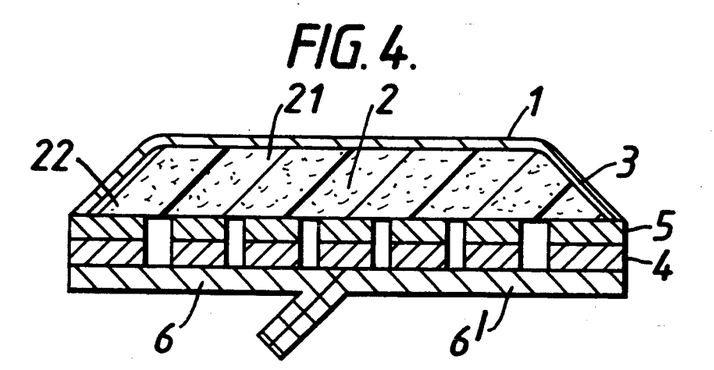
FIG. 4 is a schematic cross-sectional view of another embodiment of the present invention.
Figure 5A:
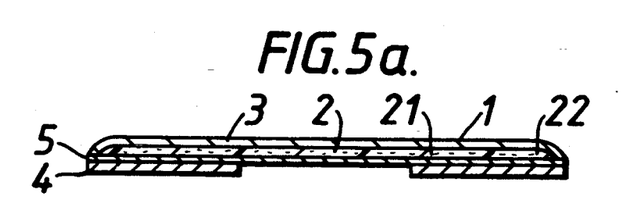
FIG. 5a is a schematic cross-sectional view of another embodiment of the present invention.
Figure 5B:
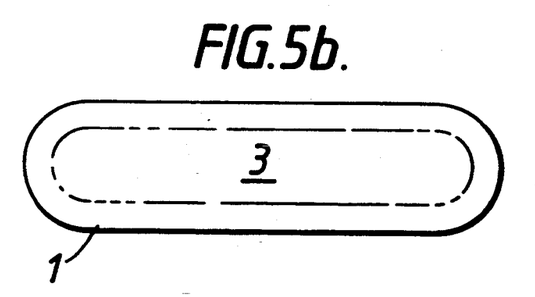
Figure 5C:
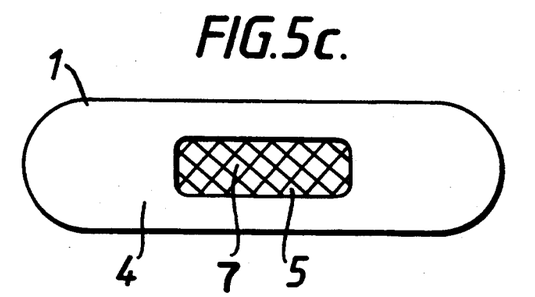
Figure 5D:
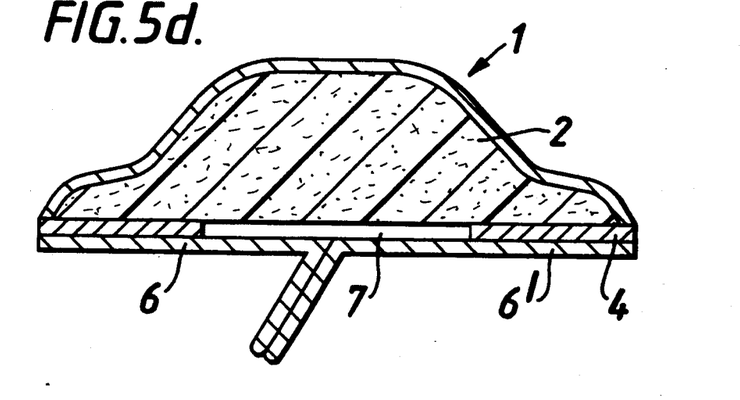
FIG. 5d is a schematic cross-sectional view of another embodiment of the present invention.

In the embodiment shown in FIG. 2 a discontinuous layer of adhesive 4 is coated directly onto the absorbent foam 2. However, the adhesive may be formed as a discontinuous layer by coating an intermediate discontinuous layer 5 (FIGS. 1, 3 and 4) with adhesive 4 which is then laminated or bonded to the absorbent layer 2. The adhesive may be discontinuous and generally over the whole of the undersurface of the dressing (FIGS. 1, 2 and 4) or the wound dressing may be provided with a centrally located adhesive-free area 7 (FIG. 5d).

The body contacting surface of the adhesive layer 5 is covered with a pair of release protectors 6 and 6' made, for example, from silane coated paper.

Figure 11A:
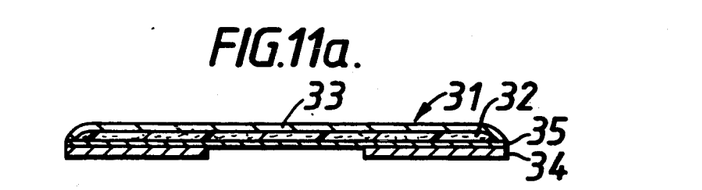
FIG. 11a is a schematic cross-sectional view of another embodiment of the present invention.
Figure 11B:
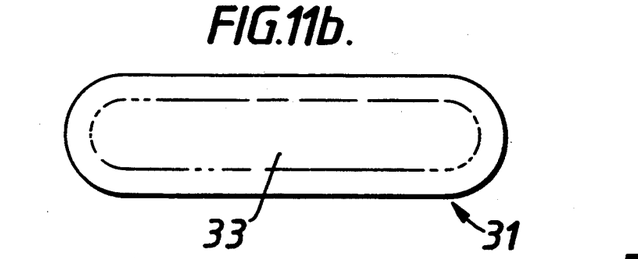
Figure 11C:
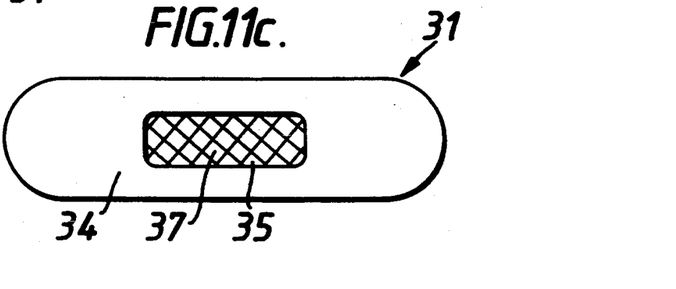

FIGS. 6 to 11a are schematic cross-sectional views of dressings of the present invention and FIGS. 11b and 11c are respectively a cross-sectional view, top view and bottom view of a dressing in accordance with the invention.

Figure 9:
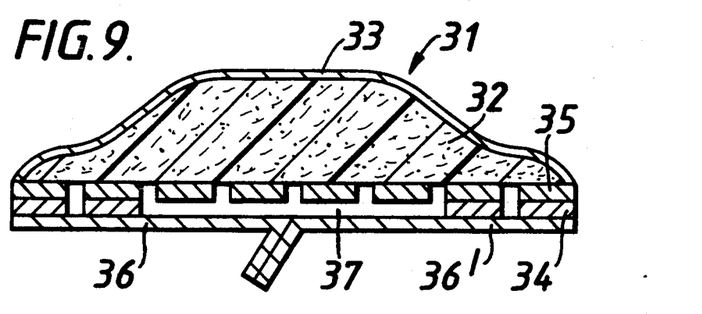
FIG. 9 is a schematic cross-sectional view of another embodiment of the present invention.
Figure 10:
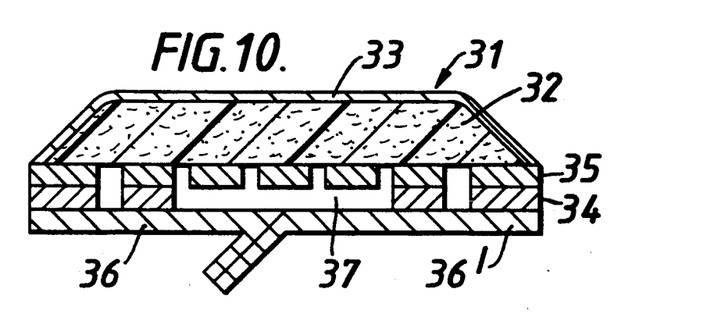
FIG. 10 is a schematic cross-sectional view of another embodiment of the present invention.

A wound dressing 31 comprises a foam absorbent layer 32. An adhesive layer 34 may be coated directly onto the foam layer (FIGS. 6 and 7) or coated onto an intermediate discontinuous layer 35 such as a net, which in turn is bonded or laminated to the foam absorbent layer 32 (FIG. 9).

Figure 6:
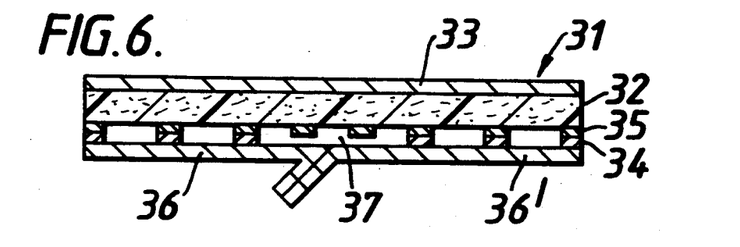
FIG. 6 is a schematic cross-sectional view of another embodiment of the present invention.
Figure 7:
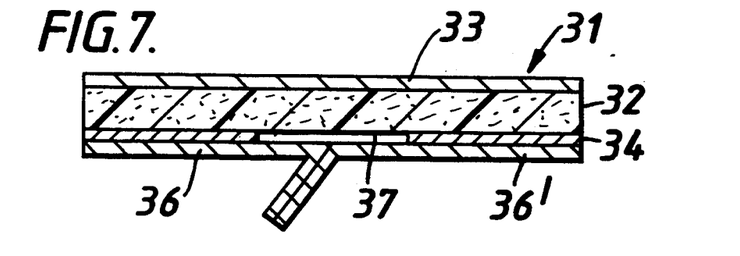
FIG. 7 is a schematic cross-sectional view of another embodiment of the present invention.
Figure 8:
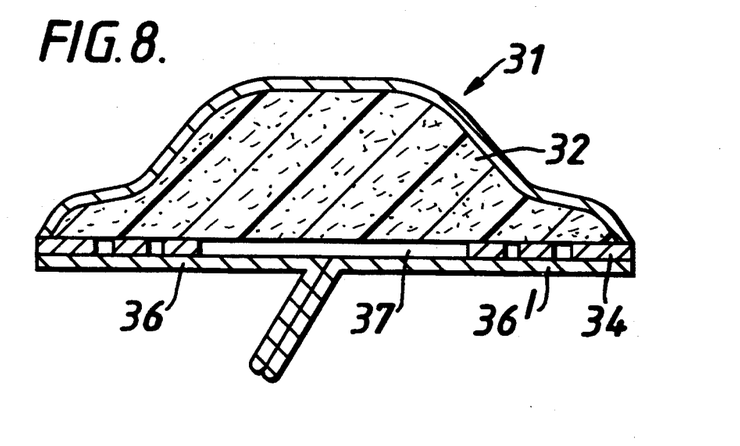
FIG. 8 is a schematic cross-sectional view of another embodiment of the present invention.

Overlying the adhesive 34 are a pair of protectors 36, 36' for the adhesive. Overlying the top surface of the absorbent layer 32 is a liquid impervious, water vapour permeable layer 33. In use the release protectors 36, 36' may be peeled away from the adhesive face 34 and the adhesive side of the dressing presented to the skin. The non-adhesive coated region, i.e., the area free of adhesive 37, is presented directly to the wound or lesion.

The invention is now illustrated by the following Examples:

EXAMPLE 1

A composite was produced by casting a polyether-polyamide copolymer (Pebax) film, a hydrophilic polyurethane foam, and a polyurethane net.

The polyurethane net was prepared according to the method described in the Examples of European Patent No. 0059048 and then crushed to a thickness of 15 $\mu$m.

The polyurethane foam was prepared by first producing a prepolymer according to Example 1 of United Kingdom Patent Specification No. 2188055 and then foaming the prepolymer in accordance with the procedure of Example 7 of United Kingdom 2188055.

The casting was carried out according to the manner described in European Patent Specification No. 0059048.

An adhesive was prepared according to Example 1 of United Kingdom Patent Specification No. 2070631 and cast onto a release sheet at a coating weight of 35 gm m². Once the adhesive had dried, rectangular areas 5 cm × 1 cm were cut out and the adhesive transfer coated onto the foam surface.

Oblate shapes measuring 6 cm × 2.5 cm were cut out, with the adhesive free areas centrally disposed to give a first-aid bandage.

The adhesive surface was then covered with release papers and the product finally cut out of the composite sheet, through the embossed region, to produce a first-aid dressing.

EXAMPLE 2

The procedure of Example 1 was repeated except that the adhesive was transfer coated directly onto the foam absorbent layer. Adhesive 'windows' measuring 25 mm × 12.5 mm were kiss-cut from the coated transfer sheet.

Once the adhesive had been applied, the film-foam-adhesive laminate was embossed and cut to form an oblate first-aid dressing measuring 63 mm × 22 mm. The edges of the dressing were embossed to provide a thin margin 1.5 mm wide around the edge of the dressing. A representation of the dressing is shown in FIGS. 6a, 6b and 6c.

EXAMPLE 3

A composite was produced by laminating a polyether-polyamide copolymer (Pebax) film, a hydrophilic polyurethane foam, and a polyurethane net through a nip defined by a rotating roller and a flat bed. The nip gap was 100 $\mu$m and the roller and bed were maintained at ambient temperature.

The polyether-polyamide film (sold under the trade name Pebax 2533 Grade SA00) was filled (50% by weight) with chalk and stretched at a draw ratio of 5:1 in both machine and transverse directions to produce a microvoided product having an upright MVTR of about 3000 and thickness between 0.04 and 0.06 mm.

The polyurethane net was prepared according to the method described in the Examples of European Patent No. 0059048 and then crushed to a thickness of 15 23 $\mu$m.

The polyurethane foam was prepared by first producing a prepolymer according to Example 1 of United Kingdom Patent Specification No. 2188055 and then foaming the prepolymer at the nip of the roller and the bed in accordance with the procedure of Example 7 of United Kingdom 2188055.

After passing through the nip, the foam is allowed to gel, and the composite embossed with an oblate punch, heated to 100° C. to define a dressing 6 cm × 2.5 cm with a periphery 1 mm thick and a central region 2.5 mm thick. The thinner peripheral region extended inwards for about 3.0 mm.

After the polyurethane had cured, a pattern spread adhesive, prepared as described in Example 4 of European Patent Specification No. 0194881, was transfer coated onto the polyurethane net side of the composite to give an adhesive coated product. The adhesive coating weight was 43 gm m² to give an adhesive layer of 27 gm m².

The adhesive surface was then covered with release papers and the product finally cut out of the composite sheet, through the embossed region, to produce a first-aid dressing.

EXAMPLE 4

The procedure of Example 3 was repeated except that the polyurethane net was omitted and the adhesive was coated directly onto the polyurethane foam by pattern spreading the adhesive. The coating weight of the adhesive over the dressing surface was 27 gm/m².

EXAMPLE 5

The procedure of Example 3 was repeated except that the moisture vapour permeable film was prepared form a blend of polyurethane and high impact polystyrene prepared in accordance with GB 2081721.A.

EXAMPLE 6

The procedure of Examples 3 and 5, respectively were repeated except that a net formed from polymer blend of Ethylene-vinyl acetate copolymer and high impact polystyrene was employed as the intermediate layer between the foam absorbent and the adhesive, instead of the Estane polyurethane net.

EXAMPLE 7

An oblate "window" dressing was produced measuring 67 mm×25 mm overall. The thickened central region measured 60 mm×19 mm.

The dressing was prepared as described in Example 3 except that the adhesive was an acrylate adhesive as described in European Patent Publication No. 99675.

Prior to coating the adhesive on the transfer sheet, red endorsing ink was mixed into adhesive mass to color it pink. The adhesive was spread onto the transfer sheet using a 200μ spreading block. Oblate windows measuring 25 mm×12.5 mm were cut from the adhesive sheet. The adhesive was then transfer coated onto the foam surface of the absorbent layer, ensuring that the window registered with the central thickened region. The non-adhesive area of the dressing was clearly visible.

What is claimed is:

1. A conformable wound dressing which comprises a polymeric foam absorbent layer, having a body facing surface, a continuous or discontinuous adhesive layer covering the body facing surface of the absorbent layer except for a wound contacting area which is free of adhesive and a layer of a liquid impervious moisture vapor permeable material disposed over substantially all of the entire surface of the absorbent layer opposite the body facing surface, wherein the adhesive layer is confined to the edges of the absorbent layer and more than 40% of the absorbent layer is free of adhesive, and wherein the thickness of the absorbent layer at two opposed margins is substantially less than the thickness of the absorbent layer between the margins.

2. A wound dressing according to claim 1 wherein more than 50% of the absorbent layer is free of adhesive.

3. A wound dressing according to claim 2 wherein more than 85% of the adhesive layer is free of adhesive.

4. A wound dressing according to claim 2 wherein the adhesive free area is centrally located on the body facing surface of the absorbent layer.

5. A wound dressing according to claim 4 wherein the adhesive layer is a continuous one.

6. A wound dressing according to claim 4 further comprising a release coated protector on the adhesive surface of the dressing.

7. A wound dressing according to claim 2, said wound dressing having a moisture vapor transmission rate of at least 300 grams/m²/24 hrs. at 37.5° C. at 100% to 10% relative humidity difference.

8. A wound dressing according to claim 7, said wound dressing having a moisture vapor transmission rate of at least 500 grams/m²/24 hrs. at 37.5° C. at 100% to 10% relative humidity difference.

9. A wound dressing according to claim 1 which further comprises a discontinuous intermediate layer coextensive with the absorbent layer disposed between the absorbent layer and the adhesive layer.

10. A wound dressing according to claim 9 wherein the adhesive layer is a discontinuous layer.

11. A wound dressing according to claim 9 wherein the adhesive layer forms discontinuities which register with the discontinuities of the intermediate layer.

12. A wound dressing according to claim 9 wherein the intermediate discontinuous layer is in the form of a net.

13. A wound dressing according to claim 12 wherein the net is a polyurethane net.

14. A wound dressing according to claim 1 wherein the polymeric foam is made from a hydrophilic polymer 15. A wound dressing according to claim 1 wherein the polymeric foam is a polyurethane foam.

16. A wound dressing according to claim 1 wherein the adhesive is colored.

17. A wound dressing according to claim 1 wherein the absorbent layer contains a therapeutically effective amount of medicament.

18. A wound dressing according to claim 9 wherein the discontinuous intermediate layer contains a therapeutically effective amount of medicament.

19. A wound dressing according to claim 1 wherein the adhesive free area is located on the thicker portion of the body facing surface of the absorbent layer.

20. A wound dressing according to claim 19 wherein the adhesive layer is a continuous one.

21. A wound dressing according to claim 19 further comprising a release coated protector on the adhesive surface of the dressing.

22. A wound dressing according to claim 1 wherein the thickness of the absorbent layer at the margins is less than half the thickness of the absorbent layer between the margins.

23. A wound dressing according to claim 18 wherein the thickness of the absorbent material between the margins is up to 2.5 mm.

24. A wound dressing according to claim 1 wherein the liquid impervious moisture vapor permeable material is a polyurethane film.

25. A method of treating a wound which comprises applying to the wound a wound dressing according to claim 1 until the wound has healed sufficiently to remove the wound dressing.

* * * * *